United States Patent [19]

Rines

[11] Patent Number: 6,077,703
[45] Date of Patent: Jun. 20, 2000

[54] METHODS FOR ISOLATION OF PENICILLIUM MOLDS FROM ARTEMISIA PLANT MATERIAL

[75] Inventor: Robert H. Rines, Concord, N.H.

[73] Assignee: Academy of Applied Science (Division of Allor Foundation), Concord, N.H.

[21] Appl. No.: 09/224,551

[22] Filed: Dec. 31, 1998

[51] Int. Cl.$^7$ ...................................................... C12N 1/14
[52] U.S. Cl. ..................................... 435/256.3; 435/254.1; 435/933
[58] Field of Search ............................... 435/256.3, 254.1

[56] References Cited

U.S. PATENT DOCUMENTS

| | | | |
|---|---|---|---|
| 3,992,523 | 11/1976 | Loud et al. | 424/114 |
| 5,276,005 | 1/1994 | Lorina et al. | 504/118 |
| 5,792,726 | 8/1998 | Lorina et al. | 504/116 |

OTHER PUBLICATIONS

Afifi et al., Egypt. J. Bot. 1977, vol. 20, No. 2, pp. 121–126.
Smith G. In: Smith's Introduction to Industrial Mycology. Seventh Edition. John Wiley & Sons. New York. 1981, p. 363.
Sikyta B. In: Methods in Industrial Microbiology. Ellis Horwood Limited. England. 1983. pp. 38–39.
ATCC Catalogue of Fugi/Yeasts. 17 th edition, 1987, pp. 259, 261 and 414.
Tantaoui–Elaraki et al., J.Essent. Oil Res., Sep./Oct. 1993, vol.5, No. 5, pp. 535–545.
Ceruti et al., Allionia (Turin), 1982, vol. 25, pp. 5–8.

*Primary Examiner*—Irene Marx
*Assistant Examiner*—Vera Afremova
*Attorney, Agent, or Firm*—Rines and Rines

[57] ABSTRACT

A method of inducing accelerated and increased mold yields from Artemesia and similar high temperature water extracts thereof in very thin shallow standing planar solution layers exposed to daylight; in particular, molds yielding *Pennicillium rinseseum* and/or *Penicillium allorenses*.

6 Claims, No Drawings

METHODS FOR ISOLATION OF PENICILLIUM MOLDS FROM ARTEMISIA PLANT MATERIAL

The present invention relates to Penicillium type molds, cultures, organisms, strains and other derivatives therefrom, hereinafter sometimes generically referred to as "molds", being more particularly directed to inducing increased mold yields from Artemesia type plants and the like, and, in particular, those developing *Penicillium rinseseum* and *Penicillium allorenses* as described in U.S. Pat. No. 3,992,523, of applicant's common assignee, the Allor Foundation, and samples of which Penicilliums have been deposited at the American Type Culture Collection under accession numbers 20398 and 20399, respectively.

BACKGROUND OF INVENTION

While the discovery of *Penicillium rineseum* and *Penicillium allorenses* with their uncustomary antibiotic property, particularly in mixture, of a synergistic efficacy against a wide spectrum of both gram negative and gram positive bacteria, evoked some interest in academic research circles, the difficult, miniscule, and sometimes inconsistent yields then inducible from dried Artemesia plants by the distilled boiling water flask steeping and then separation technique described in said patent, did not provide encouragement for ultimate commercialization—particularly since combinations of other antibiotics were available, though not providing these results in a single Penicillium type product, nor from a single and common mold-inducing process.

With the widespread use and perhaps over-use of penicillium and related antibiotic products over some decades, however, a dilemma has developed and is continuing developing from the growing mutation or other resistances to such antibiotics by microbes and the like that earlier had readily succumbed to such penicilliums. The defense mechanism of organisms to the wide and often indiscriminate use of bactericidal agents tends to react by developing mutation strains resistant to the activity of the agent. Resort to the development of new types of antibiotics is thus in full sway and at large cost and with frustrating delay.

Since *Penicillium rineseum* and *Penicillium allorenses* and their mixture is so biochemically and culturally distinct from their closest know Pencilliums, as set forth in said patent (Tables 1, 2 and 3, thereof, incorporated herein by reference) and, even more particularly, their size is so spectacularly smaller, as shown in the photographs of the drawings and the measurements in the Tables, they appear to provide interesting and perhaps increased promise against mutating microorganisms that are showing resistance to larger and biochemically distinct Penicilliums currently in use. Again, however, there is the practical drawback of inadequate practical and consistent yields by the mold-inducing process described in said patent.

Underlying the present invention, however, is believed to be a breakthrough discovery of how, immeasurably and reproducably, greatly to increase such yields, and to do so with an extremely inexpensive technique that does not even require elevated temperatures or restricted or sensitive environments—but only about room temperature and, at times, some daylight.

OBJECTS OF INVENTION

A principal object of the invention, accordingly, is to provide a new and improved method of increasing reproducible and sizable yields of such molds from Artemesia and similar plant extracts.

A further object is to provide such a technique that simultaneously provides yields of both *Penicillium rineseum* and *Penicillium allorenses*, and in combination.

Other and further objects will be explained hereinafter and are more particularly delineated in the appended claims.

SUMMARY

In summary, however, in one of its aspects, the invention embraces a method of inducing molds for deriving *Penicillium rineseum* and *Penicillium allorenses* from Artemesia plant extract solutions, that comprises, spreading, and containing a thin planar layer of the extract solution on a flat surface open to the atmosphere, and exposing the layer to daylight at room temperature over a period of a few days to induce the formation of mold spores and clusters on the planar layer.

Preferred and best mode techniques and products resulting therefrom are later described in detail.

PREFERRED EMBODIMENT(S) OF INVENTION

While many plants of the Artemesia family have been recognized for their anti-microbial effects, including, for example, *Artemesia princeps, Artemiesia arbothanium*, Absenthium, Vulgaris, etc., particularly wide-spectrum and powerful activity has been noted in the species *Artemesia aborescens*, and to a lesser extent in *Artemesia tridentata* as described, for example, in U.S. Pat. Nos. 5,276,005 and 5,792,726, also of common assignee, the Allor Foundation. The use of elevated-temperature-derived water extracts of the dried plant material (about 100° C.) is described in said patents for use as plant nutrients and for anti-microbial purposes. A preferred extraction ratio of dried plant material-to-water of about 3–5 ounces of dried plant material to 2–5 gallons of water is therein described. The results of the earlier U.S. Pat. No. 3,992,523 were also obtained principally with the former species.

It has now been discovered that, instead of trying to induce mold in such a plant extract produced by steeping in boiling water through incubating the solution in closed flasks, with the before-described inadequate yields, a remarkable avalanche of accelerated mold inducement surprisingly occurs in only a few days if the solution is spread and confined as a uniform thin layer on an open tray, with the planar liquid layer totally exposed to the air and daylight and at room temperature, and preferably with a "catalyzing" piece or few pieces or bits of the original dried plant material from which the extract was made, retained at the bottom, but totally covered by the thin liquid extract layer.

For the preferred case of Artemesia aborescens, well-defined characteristic mold spores are thus readily induced and over the principal planar area of the solution, (having the cultural characteristics outlined in said Table 2 when later incubated in such agars), and as distinguished from the almost trivial occasional mold spot achievable in solutions in flasks or bottles, or even in open containers with more substantial depth of solution, and/or absent some "catalyzing" solid plant material placed on the bottom, as will now be described.

As a first example, it was found specifically that the fastest well-defined uniform mold spores or clusters were inducible at room temperature over four days, with the water-extract solution spread and resting as a still, confined planar layer upon a flat open daylight-exposed aluminum tray with a thin shallow depth of about 0.6 cm or less. For substantially greater depths, much fewer and less distinct spores were found to be created, and for depths greater than about 1.2 cm, often no distinct mold spores developed whatsoever, and ultimately a non-descript cloudy film would form as a covering. This same cloudy film also formed in a closed light-transparent flask or jar.

In further tests to determine the effect of the daylight, with the tray covered, but open to air, cobwebs like spun cotton candy, not characteristically mold sporulating spots were formed, and/or cloudy patches.

Such patches, and ill-defined mold spores, were also observed to form when the tray was placed in the dark over the same time period.

Similar mold inducement in about 0.5–0.6 cm layer of Artemesia tridentata extract was also observed under the above conditions, though in smaller yield, perhaps attributable to the age and small quantity of the available dried plant sample for this test.

As still another example, with the open-tray, small-depth layer of cross dimension large compared to the solution depth, daylight standing was repeated for filtered Artemesia aborescens plant extract solution in three identical circular tray compartments of about 6 cm in diameter, each with about 0.6 cm depth of shallow uniform layer of the solution at the start, but with some evaporation over the four day period. A maximum of 5 well-defined mold sporulating spots of average diameter of about 0.5 cm were developed.

At the same time, an identical test was started to verify the effect of the before-mentioned "catalyzation"; by keeping a few small pieces of the plant material (up to 2–3 tablespoons of plant pieces) submerged at the bottom of the trays. With the same set up as in the immediately preceding paragraph, but using two such circular trays, more copious mold inducement was strikingly obtained, with well-defined mold sporulating spots or clusters of from 0.3 to 1.5 cm in diameter induced in one tray (as well as 6 additional somewhat less defined spores), and well-defined clusters in the other tray of from 0.2 to 1.5 cm (and with 4 more fuzzy spores) over the same time period. More than half the surface area, moreover, was covered with this high yield of mold clusters.

In still a further test, the plant material was also left in the bottom of a covered, but not sealed, pair of similar circular trays—one with a shallow initial depth of 0.6 cm and the other of 1.3 cm depth of the plant extract solution. Two very irregular spores developed in the shallow solution tray, but only "cobwebs" and fuzzy spores were produced in the deeper solution tray, again indicating the before-mentioned significance of the thin shallow depth.

Plant material at the bottom of the closed flask or jar with the deeper solution produced little detectable mold inducement effect—two very small spore spots.

From the above, accordingly, it has been considered that, in accordance with the discovery underlying this invention, the greatest and most reproducable yield results can be obtained with a quiescent thin or shallow flat layer of the plant material extract solution (preferably less then about 0.6 cm in depth), open and exposed to daylight at about room temperature, and preferably with a small piece(s) or bit of the solid plant material submerged at the bottom and covered by the solution as a mold-inducing "catalyst".

The same Penicillium rineseum and Penicillium allorenses cultural characteristics noted in Table 2 of said U.S. Pat. No. 3,992,523 were observed in the molds produced by the process of the present invention. A check on the antimicrobial efficacy was made following 3 weeks of incubation of the molds at 22° C. on malt extract agar, placed on the surface of a Mueller Hinton medium plate which was swabbed with an exemplary test bacterium of proteus vulgares ( and also e. coli), and incubated for 24 hours at about 37° C. A 2–3 mm zone of inhibition was obtained.

As earlier noted, the mold-inducing methodology of the invention appears generically useful for Artemesia and similar type plant extracts, and further modifications will occur to those skilled in this art, such being considered to fall within the spirit and scope of the invention as defined claims.

What is claimed is:

1. A process of isolating Penicillium rineseum, Penicillium allorensis or a mixture thereof comprising:

providing an aqueous solution of boiled dried plant material obtained from a plant selected from the group consisting of Artemisia arborescens and Artemisia tridentata;

placing the aqueous solution of the boiled dried plant material as a thin planar layer within a shallow open tray having a cross-dimension larger than the depth, wherein the depth is less than about one centimeter;

incubating the shallow open tray at room temperature and at daylight for several days to yield growth of Penicillium rineseum, Penicillium allorensis or a mixture thereof, and recovering Penicillium rineseum, Penicillium allorensis or a mixture thereof from the aqueous solution.

2. The method as claimed in claim 1 wherein one or more pieces of the boiled dried plant material is placed at the bottom of the tray, totally covered by the aqueous solution during the incubation period.

3. The method as claimed in claim 2 wherein the Artemesia species is Artemesia arborescens.

4. The method as claimed in claim 2 wherein the Artemesia species is Artemesia tridentata.

5. The method as claimed in claim 2 wherein the depth of the aqueous solution is less than about 0.6 centimeter.

6. The method as claimed in claim 2 wherein aqueous solution is prepared by boiling dried plant material at about 100° C. with the ratio of plant material-to-water selected from about 3–5 ounces to 2–5 gallons.

\* \* \* \* \*